(12) United States Patent
Levine et al.

(10) Patent No.: US 10,201,408 B2
(45) Date of Patent: Feb. 12, 2019

(54) DISPENSING VIAL

(71) Applicant: JBL Radical Innovations, LLC, New York, NY (US)

(72) Inventors: Jonathan B. Levine, Purchase, NY (US); Bo Tao, Chino (CH)

(73) Assignee: JBL RADICAL INNOVATIONS, LLC

( * ) Notice: Subject to any disclaimer, the term of this patent is extended or adjusted under 35 U.S.C. 154(b) by 767 days.

(21) Appl. No.: 14/597,535

(22) Filed: Jan. 15, 2015

(65) Prior Publication Data

US 2016/0206417 A1 Jul. 21, 2016

(51) Int. Cl.
| | |
|---|---|
| *A46B 11/00* | (2006.01) |
| *A45D 34/04* | (2006.01) |
| *A47L 23/05* | (2006.01) |
| *A45D 19/02* | (2006.01) |
| *A45D 40/26* | (2006.01) |
| *A61C 19/02* | (2006.01) |
| *A61C 17/02* | (2006.01) |
| *A61M 35/00* | (2006.01) |
| *A61C 5/62* | (2017.01) |
| *A61C 19/06* | (2006.01) |

(52) U.S. Cl.
CPC .......... *A61C 19/063* (2013.01); *A46B 11/00* (2013.01)

(58) Field of Classification Search
CPC .... A61C 19/063; A61C 19/06; A61M 35/006; A61M 35/003; B65D 35/08; B65D 35/02; B05C 17/00586; B05C 17/00583; A46B 11/0075; A46B 11/0041; A46B 1/00; A46B 9/005; A46B 9/02; A46B 9/021; A46B 9/04; A46B 11/0003; A61Q 11/00
USPC ................................................ 401/269, 132
See application file for complete search history.

(56) References Cited

U.S. PATENT DOCUMENTS

| | | | | | |
|---|---|---|---|---|---|
| 3,072,953 | A | * | 1/1963 | Bunke .................... | A45D 40/26 401/132 |
| 3,271,810 | A | * | 9/1966 | Raffe ...................... | A47L 23/05 215/227 |
| 3,482,920 | A | * | 12/1969 | Schwartzman ........ | B43M 11/06 401/132 |
| 4,619,009 | A | * | 10/1986 | Rosenstatter .......... | A61C 17/28 15/29 |

(Continued)

OTHER PUBLICATIONS eFunda, Properties of Silicone {Liquid silicone rubber injection molding}, retrieved on Jan. 29, 2018, http://www.efunda.com/materials/polymers/properties/polymer_datasheet.cfm?MajorID=SI &MinorID=2.*

*Primary Examiner* — Jennifer C Chiang
*Assistant Examiner* — Bradley Oliver
(74) *Attorney, Agent, or Firm* — H. Jay Spiegel (57) ABSTRACT

A dispensing vial includes three component parts, a container for an oral care formulation, an applicator tip, and a cap removably overlying the tip. The cap includes a 4-way locking system. The applicator tip has concentric rows of upwardly extending projections with the outer peripheral row of projections or nibs being longer and higher than the inner peripheral row. The projections facilitate maximum flexibility when used in the oral cavity. Preferably, the applicator projections are made of polyethylene or polypropylene with a Shore A hardness in the range of 35-75. Preferably, the oral care formulation is maintained at a viscosity in the range of 14000-21000 CP. This combination facilitates the formulation easily dispensing from the container, spreading over the applicator projections, and being applied within the oral cavity of the user.

18 Claims, 8 Drawing Sheets

(56) References Cited

U.S. PATENT DOCUMENTS

| | | | | |
|---|---|---|---|---|
| 4,974,984 A * | 12/1990 | Kafkis | ............... | A45D 34/042 401/186 |
| 5,299,877 A * | 4/1994 | Birden | ............... | A47L 23/05 401/196 |
| 6,623,201 B2 * | 9/2003 | Brumlik | ............... | A46B 11/0013 401/270 |
| 7,572,079 B2 * | 8/2009 | Wong | ............... | A46B 11/0041 222/83 |
| 7,794,168 B2 * | 9/2010 | Chang | ............... | A46B 11/0013 401/205 |
| 2003/0059247 A1 * | 3/2003 | Kandasamy | ............... | B65D 47/42 401/184 |
| 2003/0218015 A1 * | 11/2003 | Randolph | ............... | A47G 19/2272 220/212.5 |
| 2004/0172780 A1 * | 9/2004 | Benton | ............... | A46B 15/0055 15/105 |
| 2006/0285913 A1 * | 12/2006 | Koptis | ............... | A45D 40/26 401/205 |
| 2007/0201941 A1 * | 8/2007 | Koptis | ............... | A46B 7/02 401/290 |
| 2008/0128426 A1 * | 6/2008 | Rick | ............... | A61K 8/02 220/507 |
| 2008/0138145 A1 * | 6/2008 | Kwon | ............... | A45D 34/04 401/266 |
| 2008/0167590 A1 * | 7/2008 | Jon | ............... | A45D 34/042 601/160 |
| 2010/0240013 A1 * | 9/2010 | Levine | ............... | A61C 5/062 433/215 |
| 2010/0266981 A1 * | 10/2010 | Levine | ............... | A61M 35/003 433/89 |
| 2012/0175336 A1 * | 7/2012 | Miller | ............... | B65D 3/04 215/216 |
| 2013/0177870 A1 * | 7/2013 | Wang | ............... | A61C 5/064 433/90 |
| 2013/0216487 A1 * | 8/2013 | Lee | ............... | A61K 8/24 424/57 |
| 2014/0016981 A1 * | 1/2014 | Levine | ............... | A61C 19/02 401/28 |
| 2014/0064821 A1 * | 3/2014 | Price | ............... | A46B 11/0041 401/183 |
| 2014/0105667 A1 * | 4/2014 | Castex | ............... | A46B 9/021 401/129 |
| 2014/0130823 A1 * | 5/2014 | Iizaki | ............... | A45D 19/02 132/208 |
| 2015/0023721 A1 * | 1/2015 | Gieux | ............... | A45D 34/04 401/265 |
| 2015/0101630 A1 * | 4/2015 | Kodama | ............... | A45D 19/02 132/200 |
| 2016/0130002 A1 * | 5/2016 | Cuddy | ............... | B64D 11/00 267/140.13 |

* cited by examiner

DISPENSING VIAL

BACKGROUND OF THE INVENTION

The present invention improves upon the dispensing vial disclosed in co-applicant Jonathan B. Levine's U.S. patent application Ser. No. 13/546,479, filed Jul. 11, 2012, and which was published as Publication No. US 2014/0016981 A1 on Jan. 16, 2014. The prior application, above-mentioned, discloses a dispensing vial commercially described as the "G-Vial" in which a vial of tooth whitening substance is hermetically sealed within a chamber by a foil seal and a piercing element permits the seal to be broken to allow the tooth whitening gel to be dispensed on the teeth of the user using a comb-like applicator. A removable limit stop precludes the seal from being pierced until the limit stop is removed, thereby allowing a piercing element to pierce the seal.

While this arrangement has proven effective in storing and dispensing tooth whitener onto a user's teeth, Applicants found that simplifying the design and providing a more effective applicator would enhance the whitening process, and that a simplified design could also be used to dispense breath freshener and desensitizing substances.

Additionally, Applicants concluded that providing a specific relationship between the viscosity of the tooth whitening substance and the flexibility of the applicator could enhance the effectiveness of applying a tooth whitener to the user's teeth, and that an applicator tip designed to be anatomically compatible with different areas of the oral cavity could facilitate use in dispensing other oral care substances such as breath fresheners, tooth desensitizing substances, gum treating medications, and remineralizing products. With these thoughts in mind, the present invention was developed.

Applicants make reference to the following prior patents of co-inventor Jonathan B. Levine: U.S. Pat. Nos. 7,201,577; 7,597,497; 8,262,306; 8,262,390; 8,267,609; 8,398,324; and 8,419,306. Each of these patents discloses and claims a dispensing device designed to dispense substances including tooth whitening gels. However, none of these references teaches or suggests the particular applicator structure or relationship between viscosity of an oral care treatment gel and flexibility of the applicator.

SUMMARY OF THE INVENTION

The present invention relates to an improved dispensing vial. The present invention includes the following interrelated objects, aspects and features:

(1) In a first aspect, the present invention includes three component parts, a container sized and configured to receive and store a dose of tooth whitening gel or other oral care formulation, an applicator tip sealing a chamber within the container that stores the tooth whitening gel, the tip including an applicator, and a cap removably overlying the tip and a neck portion of the container. The container includes two arcuate "wings" provided to allow gripping of the container. These "wings" are similar to analogous structure disclosed in applicant Levine's Published Application No US 2014/0016981 A1.

(2) Above the chamber within the container is a neck having two diametrically opposed radially outwardly extending ribs and at the bottom of the neck two opposed upstanding tabs, all for a purpose to be described in greater detail hereinafter. The upper extremity of the neck has external threads for a purpose to be described in greater detail hereinafter. Additionally, approximately midway up the neck from the chamber, a horizontally disposed radially outwardly extending annulus is provided, also for a purpose to be described in greater detail hereinafter.

(3) The applicator tip has internal threads meshing with the external threads on the neck of the container so that the tip may easily be screwed onto the neck of the container to seal the contents of oral care substance contained within the chamber of the container. The applicator tip includes an opening that is surrounded by an applicator.

(4) The applicator tip has at its upper end an applicator comprising concentric rows of upwardly extending projections or nibs with the outer peripheral row of projections or nibs being longer and higher than the inner peripheral row. Each of the projections or nibs is slightly tapered from a wider portion adjacent their attachment to the tip to a slightly thinner configuration at their extreme ends. Each of the projections or nibs has approximately a circular cross-section. The described configuration of the projections or nibs is designed to facilitate their maximum flexibility when used and provide material memory to restore them to their original positions. The projections or nibs are preferably integrally molded with the rest of the tip.

(5) Overlying the applicator tip is a cap designed to cover the applicator tip and also seal the contents of the chamber until the user is ready to dispense an oral care formulation. For these purposes, the cap has a pair of opposed elongated recesses that slide down over the vertically extending ribs of the applicator tip to align the cover in its installation on the container. At the bottom ends of these elongated recesses, generally semi-circular cutouts enmesh with the upstanding tabs on the container to assist in locking the cover on the container. Additionally, within the cap, a horizontal peripheral recess engages the annulus of the neck of the container to further lock the cap over the neck of the container. Finally, within the cap, a downwardly extending shaft is included that extends into the opening and passage in the tip when the cap is installed thereover. The outer dimensions of the shaft correspond to the inner dimensions of the opening and associated passageway so that the oral care formulation is hermetically sealed within the chamber of the container. Preferably, the material of the applicator tip and thus of the inner walls of the passage is slightly softer than that of the cap and its shaft. Thus, when the shaft is inserted in the passage, the passage walls slightly flex to enhance the seal with the shaft while this interaction enhances frictional retention of the shaft in the passage.

(6) The 4-way locking mechanism of the cap over the container and tip, consisting of an annulus and recess, the ribs and recesses, the cutouts and tabs and the shaft and passage ensure that the cap is properly installed over the tip and container while the shaft with its interference fit within the passage in the tip ensures maintenance of freshness of oral care formulation until it is time to dispense it.

(7) Applicants have discovered an effective synergy between the viscosity of the oral care formulation and the durometer of the applicator projections or nibs that facilitates quite effective dispensing and application on a user's teeth. In the preferred embodiment of the present invention, the applicator projections or nibs are made of polyethylene or polypropylene with a degree of stiffness defined by a Shore A hardness in the range of 35-75. The tooth whitening gel is maintained at a viscosity in the range of 14000-21000 CP. Applicants have found that so long as the resiliency of the nibs is maintained within the Shore A hardness range described above and the viscosity of the oral care formulation is maintained within the range above-described, the formulation may be easily dispensed through the opening within the neck of the container, spread over the applicator projections or nibs, and be easily and effectively coated on the teeth, gums, tongue or other oral cavity areas of the user with the user being able to easily control the application process.

As such, it is a first object of the present invention to provide an improved dispensing vial.

It is a further object of the present invention to provide such a vial in which applicator projections or nibs are manufactured within a desired range of flexibility and an oral care formulation dispensed by the inventive device is maintained within a desired viscosity range.

It is a still further object of the present invention to provide an improved dispensing vial with a cap, tip and container using a 4-way sealing system ensuring firm attachment and retention.

It is a yet further object of the present invention to provide such an improved dispensing vial in which a cap includes a downwardly extending shaft entering an opening and passage in the applicator tip of the device to hermetically seal a chamber containing a dose of oral care formulation, given the greater resiliency of the passage walls as compared to the outer walls of the shaft.

It is a still further object of the present invention to provide such an improved dispensing vial in which the applicator tip consists of two concentric rows of upwardly extending projections or nibs specifically engineered to enhance smooth application of oral care formulation on surfaces within the oral cavity of a user.

It is a still further object of the present invention to provide such an improved dispensing vial with a container having two arcuate wing-like extensions allowing easy gripping of the container for dispensing of the oral care formulation and case of removal of the cap.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figures 1, 2:
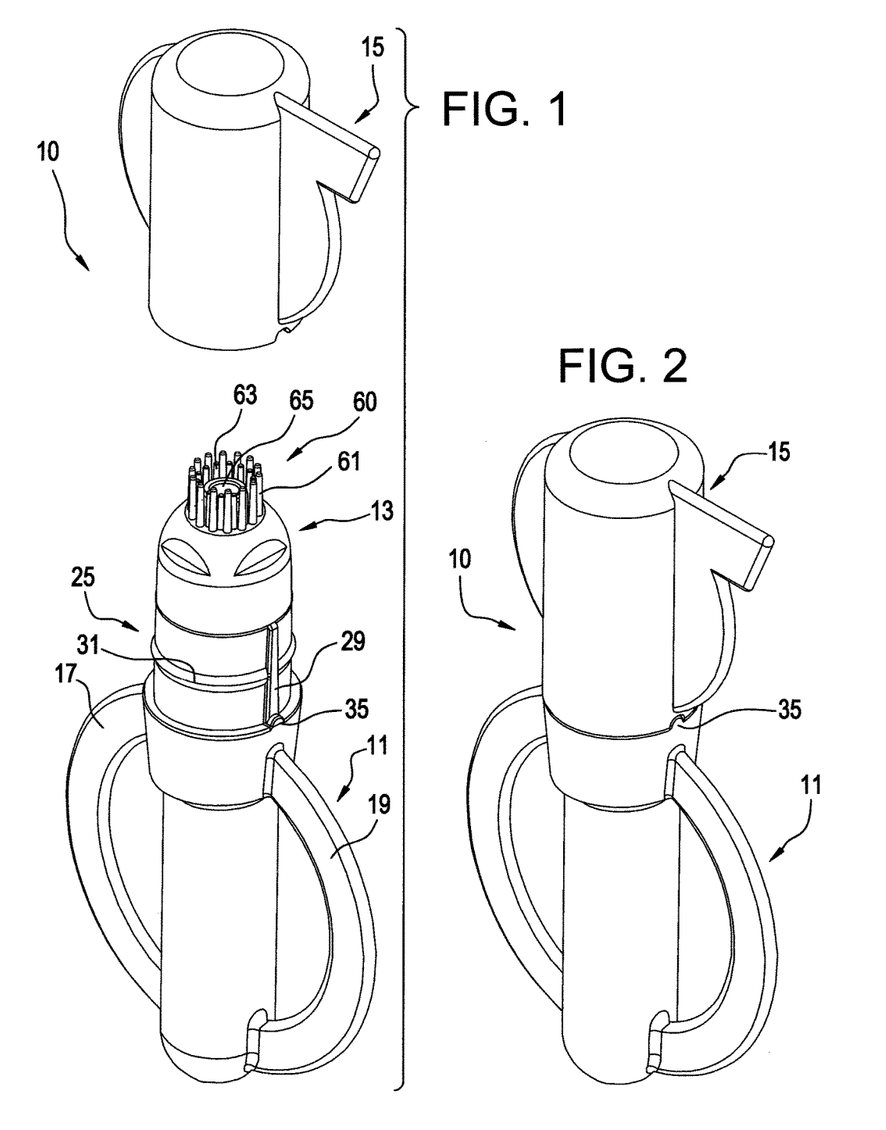
FIG. 1 shows an exploded perspective view of the improved dispensing vial of the present invention.
FIG. 2 shows a perspective view from the same perspective as that of FIG. 1 with the cover of the inventive device installed in place.
Figure 3:
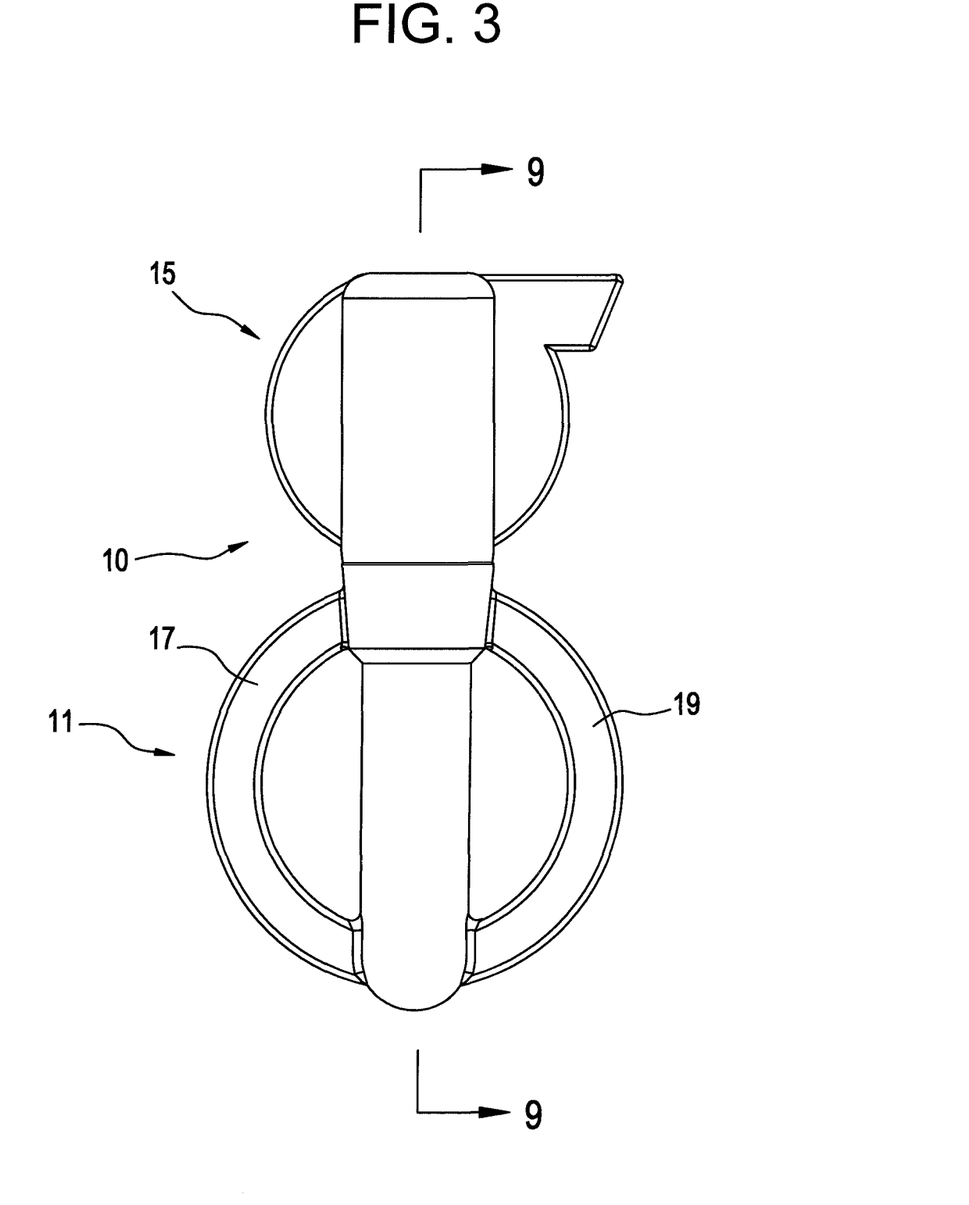
FIG. 3 shows a front view of the present invention.

With first reference to FIG. 1, the present invention is generally designated by the reference numeral 10 and is seen to include a container 11, an applicator tip 13, and a cap 15. The container 11 and the cap 15 are also visible in FIGS. 2 and 3. As seen, for example, in FIGS. 1-5, the container 11 includes two diametrically opposed gripping wings 17 and 19 which are provided to facilitate gripping of the container 11.

Figure 8:
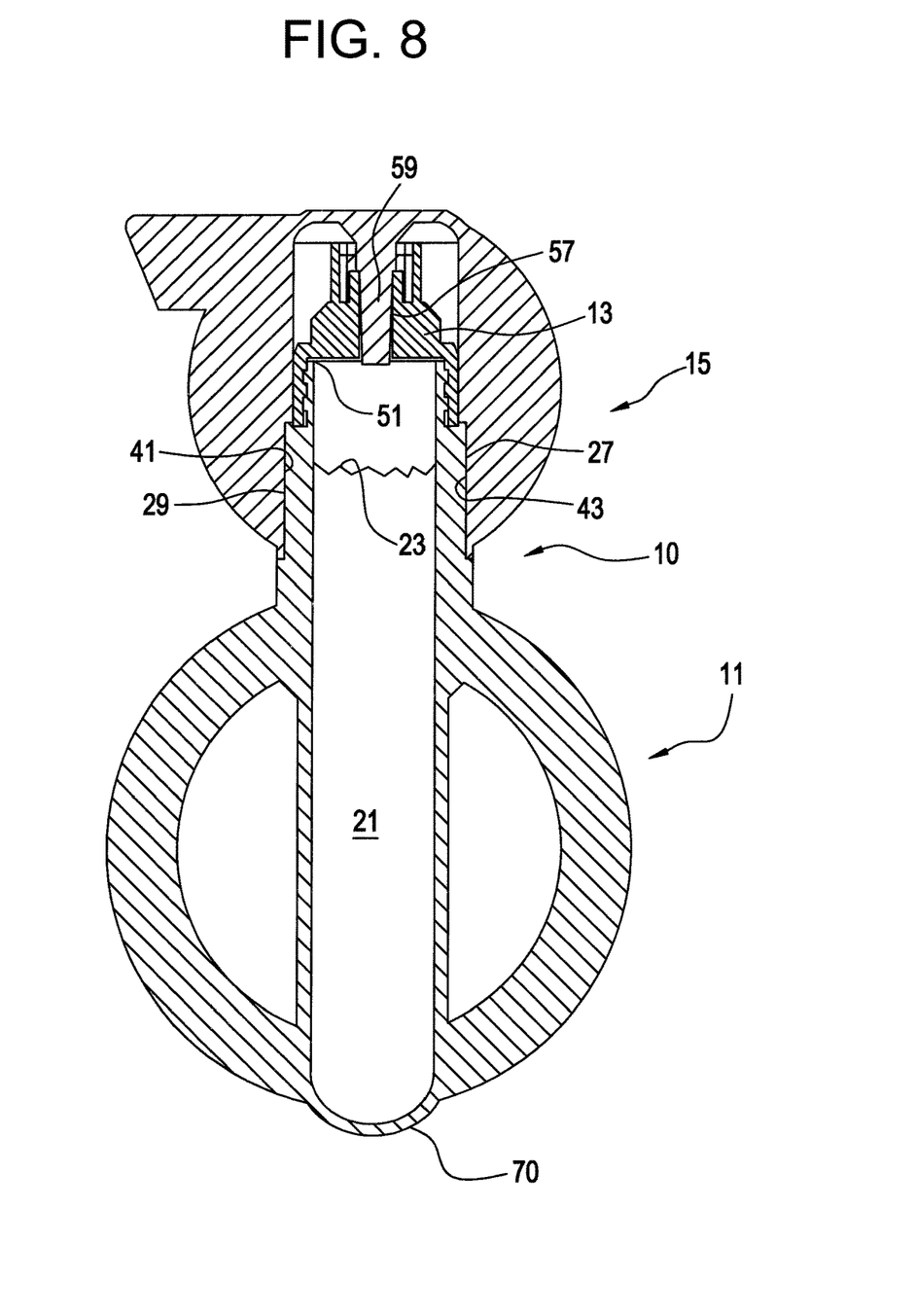
FIG. 8 shows a cross-sectional view along the line 8-8 of FIG. 7.
Figure 9:
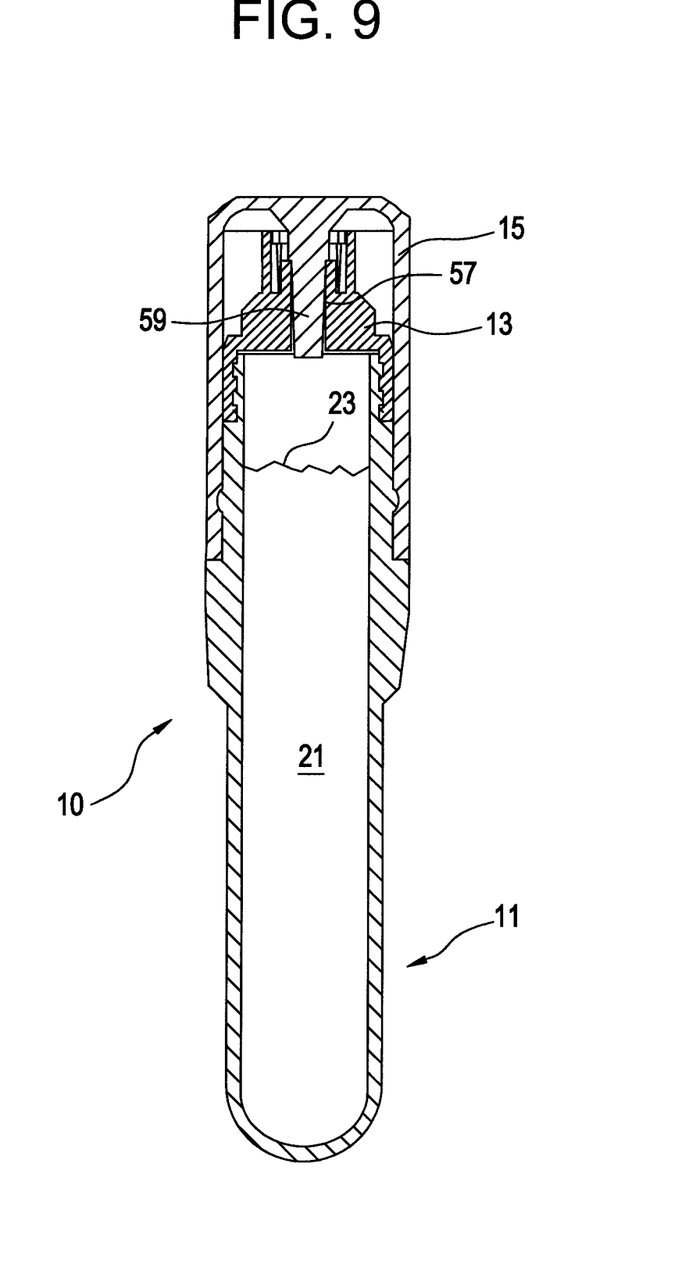
FIG. 9 shows a cross-sectional view along the line 9-9 of FIG. 3.

As seen in FIGS. 8 and 9, the container 11 includes an internal chamber 21 sized to receive a dose of tooth whitening gel 23 or other oral care formulation. The dose may provide a single application or multiple applications as desired.

Figure 4:
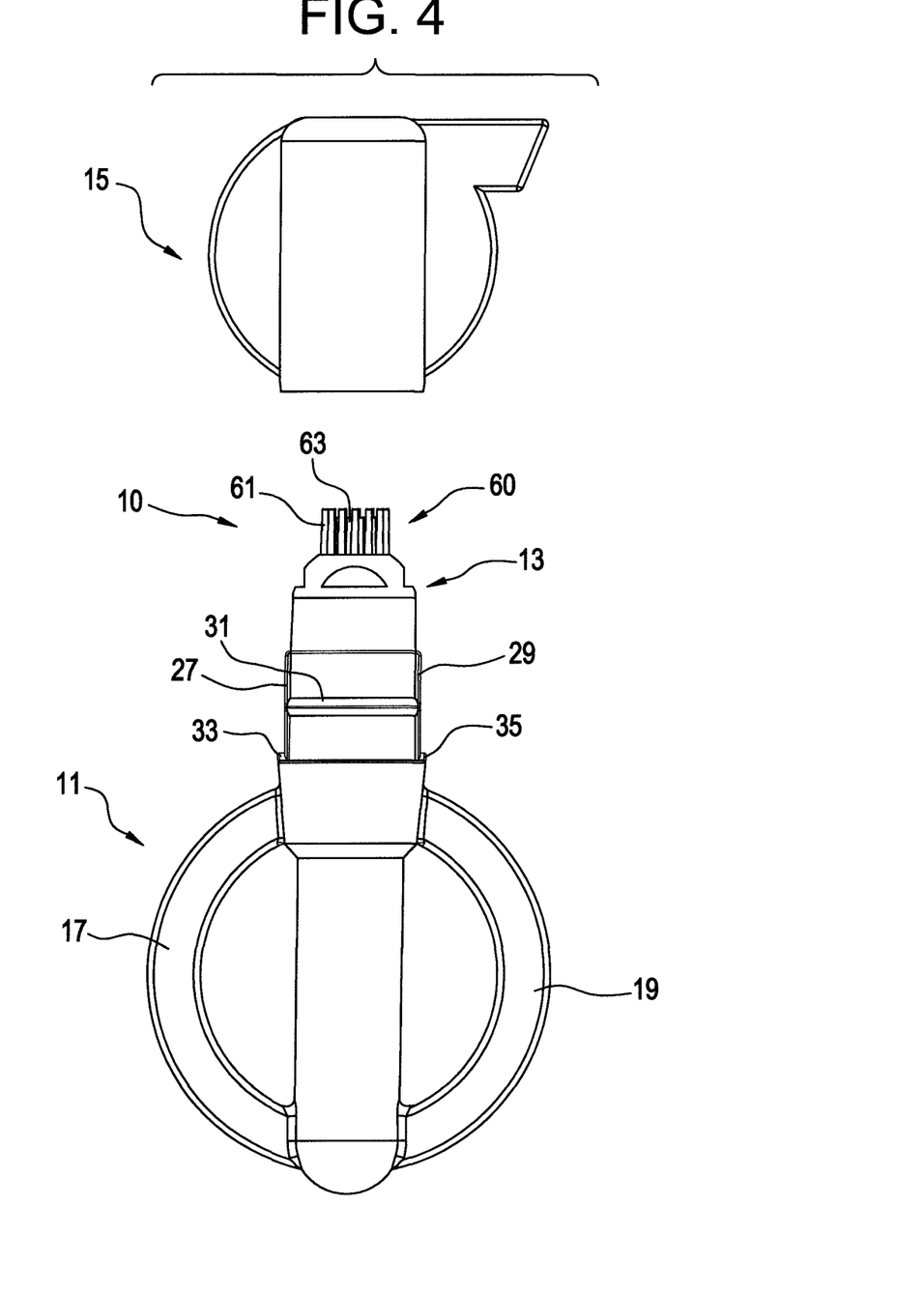
FIG. 4 shows an exploded front view of the present invention.

With reference to FIGS. 2 and 4, the present invention includes a 4-way securing apparatus for securing the cover 15 on the container 11. With reference to FIGS. 1 and 4, the container 11 has a neck 25 at an upper termination of said container which includes vertically outwardly extending ribs 27 and 29, a centrally located horizontal radially outwardly extending rib annulus 31, and two upstanding tabs 33 and 35. The applicator tip 13 includes an opening 65 (FIG. 1) and a passage 57 (FIGS. 8-9).

Figure 5:
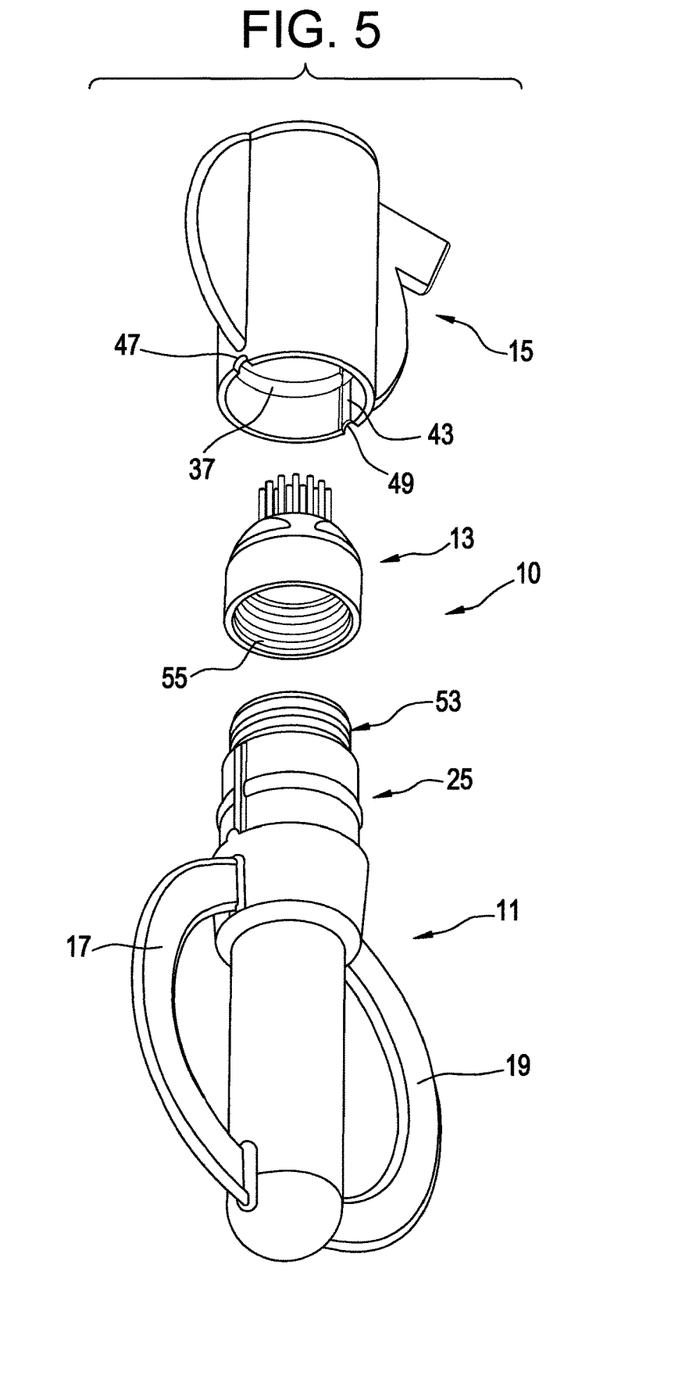
FIG. 5 shows an exploded perspective view showing all three components of the present invention separated from one another.
Figures 6, 7:
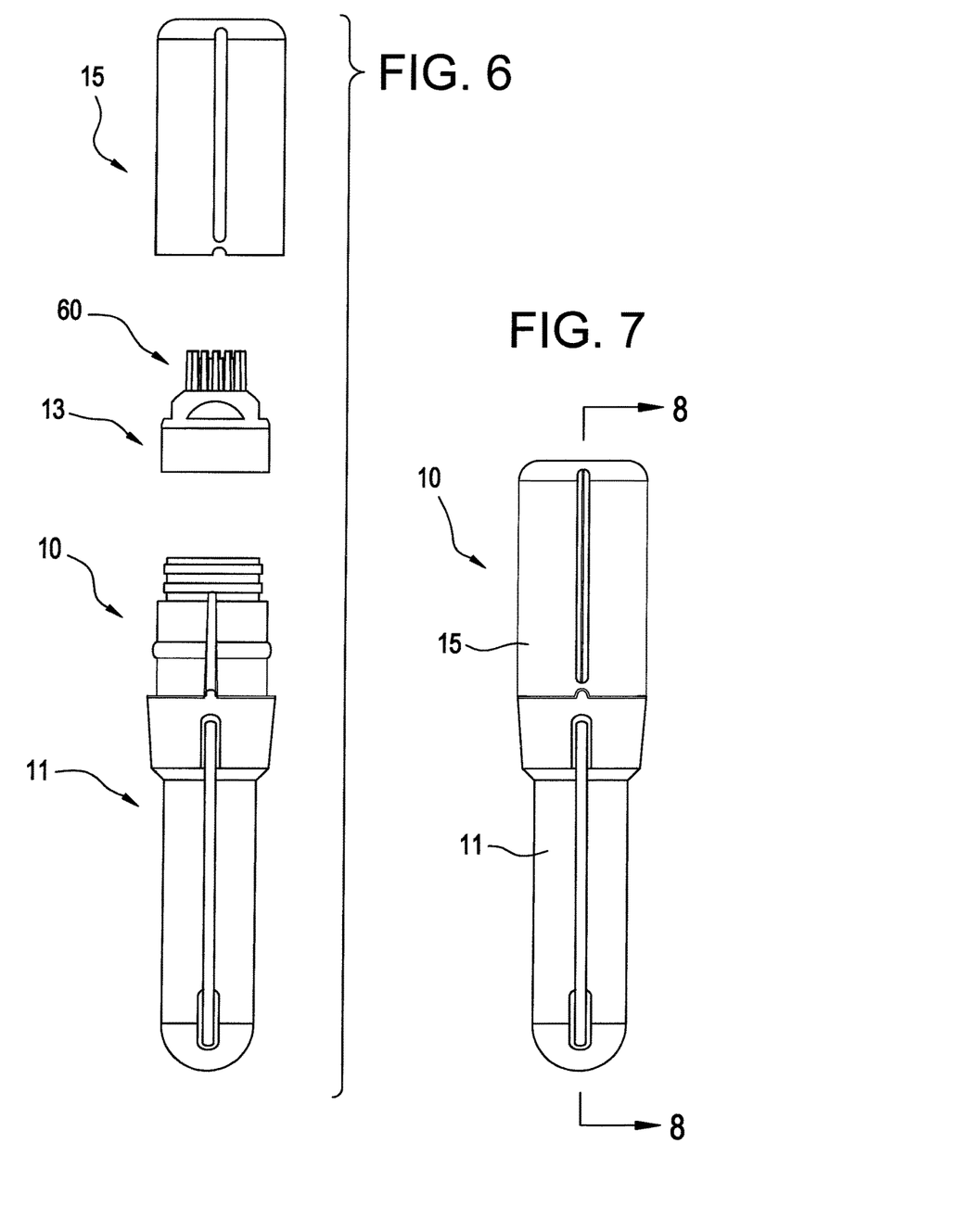
FIG. 6 shows a side exploded view of the present invention with all three components separated from one another.
FIG. 7 shows a side view of the inventive device assembled together.

As seen in FIG. 5, the cap 15 has an internal annular horizontal recess 37 designed to enmesh with the annulus 31 as a first locking mechanism. Additionally, with reference to FIGS. 5 and 8, the cap includes vertically extending recesses 41 and 43 designed to enmesh with the ribs 27 and 29 (FIG. 8). Additionally, with reference to FIG. 5, the arcuate recesses 47 and 49 overlie and engage the upstanding tabs 33, 35 (FIG. 4) to further lock the position of the cap 15 on the container 11. Finally, the shaft 59 (FIGS. 8-9) of the cap 15 enters the passage 59 in an interference fit to seal the passage 59.

The top or upper termination of the neck 25 of the container 11 includes a first opening 51 (FIG. 8) through which the tooth whitening gel 23 may be dispensed. At the top of the neck 25, external screw threads 53 are provided (FIG. 5) designed to enmesh with internal screw threads 55 within the applicator tip 13 (FIG. 5) to allow the applicator tip 13 to be screwed onto the neck 25 of the container 11.

With reference to FIGS. 8 and 9, the passage 57 extends through the applicator tip 13 below the opening 65 allowing the oral care formulation 23 to be dispensed from the chamber 21 when the cap 15 has been removed. In this regard, the cap 15 includes the downwardly extending stem or shaft 59 (FIGS. 8 and 9) that, when the cap 15 is installed over the neck 25 of the container 11, extends through the opening 65 and passage 57 to hermetically seal the chamber 21. In this regard, the outer dimensions of the stem or shaft 59 are sized and configured to create an interference fit in the opening 65 and passage 57 to ensure effective sealing of the contents of the chamber 21. Preferably, the durometer of the applicator tip is lower than that of the shaft 59 so that the inner walls of the passage 57 can flex to enhance the seal with the shaft 59.

Figure 10:
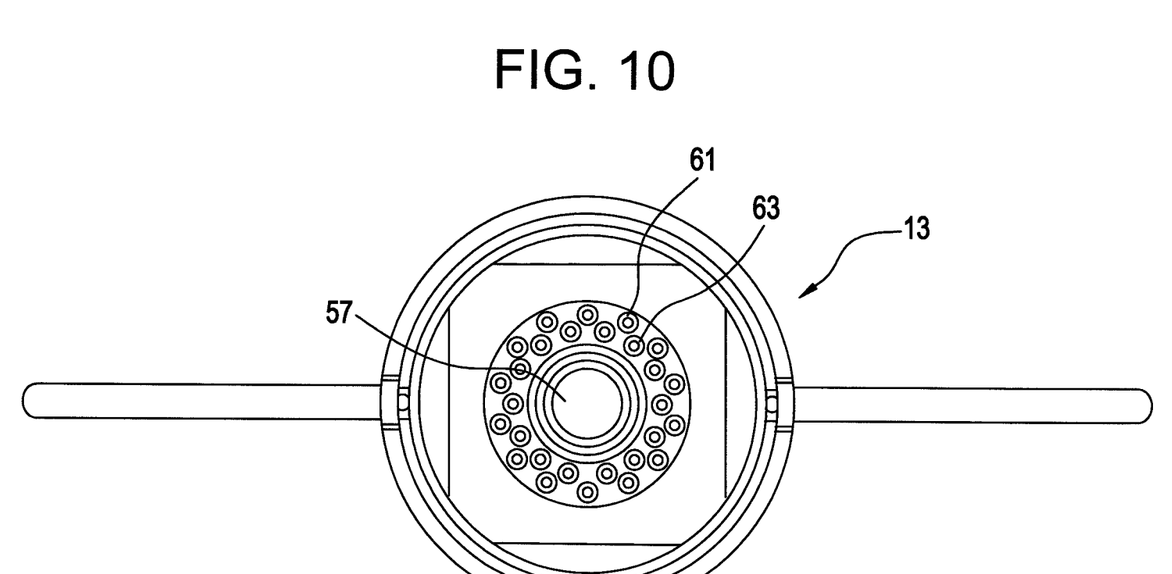
FIG. 10 shows a top view of the cap of the present invention.

With particular reference to FIGS. 1, 4 and 10, on the top of the applicator tip thereon are installed two concentric rows of projections or nibs 60 which comprise the applicator for the inventive dispensing vial 10. In these rows of projections or nibs, the outer peripheral row is circular and includes a multiplicity of projections or nibs 61, while the inner peripheral row is also circular and includes a plurality of projections or nibs 63. The projections or nibs 61 and 63 surround the opening 65 of the passage 57. As seen in FIG. 10, the projections or nibs 61 are laterally staggered with respect to the projections or nibs 63. Thus, going around the passage 57 opening 65, the projections or nibs alternate between projections or nibs 61 and projections or nibs 63.

As clearly seen in FIGS. 1 and 4, the projections or nibs 61 and 63 are slightly wider at their bases where they are attached to the applicator tip 13 than they are at their extremities remote from the applicator tip 13. In the preferred embodiment of the present invention, the projections or nibs 61 and 63 are made out of polyethylene or polypropylene, with a resiliency defined by the durometer Shore A 35-75. This range of resiliency is critical to the proper operation of the present invention. In particular, the tooth whitening gel 23 or other oral care formulation is in the range of 14000-21000 CP. Applicants have found that the combination of an oral care formulation having a viscosity at that range and applicator projections or nibs having a resiliency at the mentioned Shore A hardness range facilitates efficient transmission of the oral care formulation from the chamber 21 through the passage 7 and opening 65 and onto the projections or nibs 61, 63. Moreover, that same synergy has been found to provide effective application of a gel from the projections or nibs 61, 63 to surfaces in the oral cavity of the user. The configuration of the projections or nibs 61, 63 enhances targetability of placement of a gel on desired targeted surfaces within the oral cavity. The projections or nibs 61 and 63 are preferably formed with circular cross-sections.

Use of intermeshing screw threads to attach the applicator tip to the container avoids the need for any glue or other adhesive that can yellow over time and break down over time. Additionally, use of a screw thread allows the manufacturer to re-design the applicator tip and replace the existing applicator tip with another applicator tip for other applications that could use the same container and chamber. Such other designs might be useful to dispense substances unique for plaque removal, breath freshening, re-mineralizing of teeth or de-sensitizing of teeth. Such ability to interchange applicators will also allow the ability to dispense formulations comprised of two or more parts that are mixed just prior to application. Of course, the applicator tip shown in the drawing figures is usable to dispense a variety of oral care formulations.

The above-described viscosity range for the preferred tooth whitening gel (which can comprise a gel including a desired percentage of an active ingredient such as hydrogen peroxide, for example, up to a concentration of 9% or other known tooth whitener or other oral care formulation) can be described as extremely "thick," desirable because a relatively thick gel will better be retained on the tooth surfaces or other oral cavity surfaces such as gums or tongue where it has been applied. The diameter of the opening 65 and passage 57 are designed to facilitate easy dispensing of highly viscous gel therethrough.

Applicants note that higher percentages of hydrogen peroxide in a tooth whitening gel can cause a burning sensation on the fingers of the user if the gel accidentally engages those fingers. The inventive dispensing vial is specifically designed to allow efficient, accurate and easy dispensing of tooth whitening gel on tooth surfaces of a user while avoiding engaging the tooth whitening gel with the fingers of the user. Additionally, the rows of projections or nibs 61, 63 allow for accurate placement of the gel solely on the surfaces of the teeth so that it is possible to avoid touching the gums with the gel which can conceivably cause pain due to the potentially high concentration of active ingredient dispensed. This targetability of the applicator tip is an important aspect of the present invention. As shown in FIGS. 1 and 4, the rows of projections with the higher projections or nibs are on the outside and the lower projections or nibs are on the inside, allowing for the viscous formulation to stay up on the tip, thereby allowing the user to target the desired area with much greater accuracy. For whitening, the tooth surface is targeted; for gum health, it is the gingival sulcus interface between the gum and the tooth that is targeted; for desensitizing, it is the tooth roots that are targeted; for breath freshening, it is the tongue that is targeted.

In another advantage, the design of the container 11 and applicator tip 13 allows the chamber 21 to be filled from either the top opening 51 or through an opening (not shown) at the area of reference numeral 70 in FIG. 8, whereupon that area can be closed to seal the chamber 21. In this regard, it is possible to manufacture the inventive dispensing vial 10 by screwing the applicator tip 13 onto the neck 25 and installing the cap 15 over the applicator tip 13 before the chamber 21 is filled with tooth whitening gel 23 or other oral care formulation. In this regard, during the manufacturing process, the area designated by reference numeral 70 in FIG. 8 is open. After a desired quantity of oral care formulation is poured into the chamber 21, the bulbous area at 70 is formed to hermetically seal the chamber 21.

The components of the inventive dispensing vial 10, namely, the container 11, applicator tip 13, and cap 15 may be made of any suitable material. Preferably, they are made of an injection molded plastic able to safely receive and dispense a tooth whitening gel while not emitting any undesirable odors. Examples of such materials are polyethylene or polypropylene plastic. Preferably, the applicator tip including the projections or nibs is integrally formed in a molding process.

As such, an invention has been disclosed in terms of a preferred embodiment thereof which fulfills each and every one of the objects of the invention as set forth hereinabove, and provides a new and useful improved dispensing vial of great novelty and utility.

Of course, various changes, modifications and alterations in the teachings of the present invention may be contemplated by those of ordinary skill in the art without departing from the intended spirit and scope thereof.

As such, it is intended that the present invention only be limited by the terms of the appended claims.

The invention claimed is:
1. An improved dispensing vial in combination with a liquid contained therein, comprising:
  a) a container having an internal chamber containing said liquid to be dispensed therefrom, the liquid having a viscosity within the range of 14000 to 21000 CP, the chamber having a first opening from which the liquid may be dispensed;
  b) an applicator tip mounted on said container, said applicator tip including a passage fluidly connected to said first opening and an applicator remote from said container and comprising a plurality of concentric rows of projections surrounding a second opening at an end of said passage, said projections having a degree of stiffness defined by a Shore A hardness in the range of 35-75; and
  c) a cap overlying said applicator tip and including a shaft entering said passage to seal said passage and chamber, said cap including two vertically extending recesses, said container having two vertically extending ribs entering said recesses when said cap is placed over said applicator tip and a pair of upstanding tabs on said container, said cap having a pair of recesses receiving said tabs when said cap is placed over said applicator tip and container.

2. The combination of claim 1, wherein said container includes a pair of opposed gripping wings.

3. The combination of claim 1, wherein said container includes a neck having an upper termination at said first opening, and external screw threads surrounding said neck below said first opening, said applicator tip including internal screw threads configured to enmesh with said external screw threads to couple said applicator tip to said container.

4. The combination of claim 1, wherein said plurality of concentric rows of projections comprises two rows of projections, an inner row and an outer row.

5. The combination of claim 4, wherein projections in said outer row are longer than projections in said inner row.

6. The combination of claim 5, wherein said projections have circular cross-sections.

7. The combination of claim 4, wherein each row of projections is generally circular.

8. The combination of claim 7, wherein projections in said outer row are laterally staggered with respect to projections in said inner row.

9. The combination of claim 1, wherein said recesses and ribs are diametrically opposed.

10. The combination of claim 1, wherein said cap includes a horizontal annular recess, said container having a horizontally extending rib annulus entering said annular recess when said cap is placed over said applicator tip and container.

11. The combination of Claim 1, wherein said tabs and recesses are each diametrically opposed.

12. The combination of claim 11, wherein each said tab is located at a bottom extent of one of said vertically extending ribs and each said recess is located at a bottom extent of one of said vertically extending recesses.

13. The combination of claim 1, wherein said projections are made of a plastic material chosen from the group consisting of polyethylene and polypropylene.

14. The combination of claim 13, wherein said applicator tip including said projections is integrally formed.

15. An improved dispensing vial, comprising:
   a) a container having an internal chamber containing a liquid to be dispensed therefrom, the chamber having a first opening from which the liquid may be dispensed;
   b) an applicator tip mounted on said container, said applicator tip including a passage fluidly connected to said first opening and an applicator remote from said container and comprising two concentric rows of circular cross-section projections surrounding a second opening at an end of said passage, comprising an outer row and an inner row, projections in said outer row being longer than projections in said inner row, projections in said outer row being laterally staggered with respect to projections in said inner row, said projections having a degree of stiffness defined by a Shore A hardness in the range of 35-75; and,
   c) a cap overlying said applicator tip and including a shaft entering said passage to seal said passage and chamber, said cap including two vertically extending diametrically opposed recesses, said container having two vertically extending diametrically opposed ribs entering said recesses when said cap is placed over said applicator tip, said cap further including a horizontal annular recess, said container further having a horizontally extending rib annulus entering said annular recess when said cap is placed over said applicator tip, and further including a pair of upstanding tabs on said container, said cap having a pair of recesses receiving said tabs when said cap is placed over said applicator tip, said tabs and recesses each being diametrically opposed.

16. The dispensing vial of claim 15, wherein each row of projections is generally circular.

17. The dispensing vial of claim 15, wherein said container includes a neck having an upper termination at said first opening, and external screw threads surrounding said neck below said first opening, said applicator tip including internal screw threads configured to enmesh with said external screw threads to couple said applicator tip to said container.

18. An improved dispensing vial in combination with a liquid contained therein, comprising:
   a) a container having an internal chamber containing said liquid to be dispensed therefrom, the liquid having a viscosity within the range of 14000 to 21000 CP, the chamber having a first opening from which the liquid may be dispensed;
   b) an applicator tip mounted on said container, said applicator tip including a passage fluidly connected to said first opening and an applicator remote from said container and comprising a plurality of concentric rows of projections surrounding a second opening at an end of said passage, said projections having a degree of stiffness defined by a Shore A hardness in the range of 35-75, and said projections being made of a plastic material chosen from the group consisting of polyethylene and polypropylene; and
   c) a cap overlying said applicator tip and including a shaft entering said passage to seal said passage and chamber.

* * * * *